(12) United States Patent
Bird et al.

(10) Patent No.: US 9,883,965 B2
(45) Date of Patent: Feb. 6, 2018

(54) ATTACHMENT MECHANISM FOR OSTOMY BAGS

(71) Applicant: Welland Medical Limited, Crawley (GB)

(72) Inventors: Paul Bird, Crawley (GB); Barrie Mills, Crawley (GB)

(73) Assignee: Welland Medical Limited, Crawley (GB)

( * ) Notice: Subject to any disclaimer, the term of this patent is extended or adjusted under 35 U.S.C. 154(b) by 705 days.

(21) Appl. No.: 14/352,780

(22) PCT Filed: Oct. 19, 2012

(86) PCT No.: PCT/GB2012/000806
§ 371 (c)(1),
(2) Date: Apr. 18, 2014

(87) PCT Pub. No.: WO2013/057472
PCT Pub. Date: Apr. 25, 2013

(65) Prior Publication Data
US 2014/0249494 A1  Sep. 4, 2014

(30) Foreign Application Priority Data

Oct. 19, 2011  (GB) .................................. 1118011.4

(51) Int. Cl.
*A61F 5/449* (2006.01)
*A61F 5/443* (2006.01)
*A61F 5/445* (2006.01)

(52) U.S. Cl.
CPC .............. *A61F 5/449* (2013.01); *A61F 5/443* (2013.01); *A61F 5/445* (2013.01)

(58) Field of Classification Search
CPC combination set(s) only.
See application file for complete search history.

(56) References Cited

U.S. PATENT DOCUMENTS

| 2,675,001 | A | * | 4/1954 | Jones | A61F 5/445 604/343 |
| 2,684,676 | A | * | 7/1954 | Perry | A61F 5/445 604/344 |
| 2,759,477 | A | * | 8/1956 | Mains | A61F 5/4408 604/343 |

(Continued)

FOREIGN PATENT DOCUMENTS

| GB | 2094154 A | 9/1982 |
| GB | 2476680 A | 7/2011 |

OTHER PUBLICATIONS

Dupont Elvax Composition Information Sheet, pp. 1-4, DuPont Corp., Wilmington, DE, 2016, http://www.dupont.com/products-and-services/plastics-polymers-resins/ethylene-copolymers/brands/elvax-ethylene-vinyl-acetate.html.*

(Continued)

*Primary Examiner* — Todd J Scherbel
*Assistant Examiner* — Guy K Townsend
(74) *Attorney, Agent, or Firm* — Foley Hoag LLP

(57) ABSTRACT

An ostomy device comprises an ostomy bag; a peristomal pad with a body-side adhesive surface and at least one belt attachment means interposed between the ostomy bag and the bag-side surface of the peristomal pad, wherein the device comprises at least one skin protection means.

7 Claims, 3 Drawing Sheets

(56) References Cited

U.S. PATENT DOCUMENTS

| | | | | |
|---|---|---|---|---|
| 4,411,659 | A | * | 10/1983 | Jensen ............... A61F 5/441 604/332 |
| 4,710,182 | A | | 12/1987 | Bryson |
| 5,776,120 | A | * | 7/1998 | Shelley .............. A61F 5/445 604/332 |
| 6,863,663 | B1 | * | 3/2005 | Mills ................. A61F 5/443 604/337 |
| 2002/0026162 | A1 | * | 2/2002 | Bateman .......... A61F 5/445 604/342 |
| 2002/0032418 | A1 | * | 3/2002 | Iseke ................ A61F 5/448 604/338 |
| 2002/0088080 | A1 | | 7/2002 | Fenton |
| 2003/0225387 | A1 | * | 12/2003 | Zedlitz ............. A61F 5/441 604/385.03 |
| 2004/0230170 | A1 | * | 11/2004 | Fenton ............. A61F 5/445 604/336 |
| 2011/0165539 | A1 | * | 7/2011 | Sang ................ A61K 6/0023 433/217.1 |
| 2014/0249494 | A1 | * | 9/2014 | Bird ................. A61F 5/445 604/344 |

OTHER PUBLICATIONS

International Search Report for PCT/GB2012/000806 dated Feb. 15, 2013.

* cited by examiner

ATTACHMENT MECHANISM FOR OSTOMY BAGS

RELATED APPLICATIONS

This application is a U.S. National Stage Application of International Application No. PCT/GB2012/000806, filed Oct. 19, 2012, which claims the benefit of Application No. GB 1118011.4, filed Oct. 19, 2011; the entire contents of each of said applications is hereby incorporated in its entirety by this reference.

The present invention relates to an attachment mechanism for ostomy bags and like drainage bags, and in particular to an attachment mechanism for such bags that enables attachment of the bag to a wearer using a belt.

Ostomy bags for receiving bodily waste from colostomy or ileostomy patients are well known and a problem with such bags relates to the attachment mechanism for securing the bag in the correct and comfortable position against the body of a wearer of the bag. It is known for an ostomy bag to be a unitary, "one-piece" device wherein the pouch and adhesive faceplate are permanently joined together. Alternatively, the adhesive faceplate and the pouch can be coupled together by a user of a "two-piece" ostomy bag. Both one-piece and two-piece ostomy appliances can be used with a belt to secure the bag in place. Known means for attaching the belt to the bag have been found to cause discomfort and irritation to the wearer. A known prior art system uses a "keyhole" clip mechanism. A keyhole opening on the ostomy appliance is configured to mate with a corresponding protrusion/clip on the belt. The clip is a rigid, plastic component that presses against the wearer's skin when the appliance is attached. This causes bruising and skin damage including pressure sores, especially at the point of attachment of the belt.

European patent EP0629389 discloses a "floating" belt-attachment ring. The belt-attachment means is a relatively stiff ring which extends around the periphery of a thin, flexible, annular web. The ring is not rigidly fixed to the adhesive faceplate and the pouch, but "sits" or "floats" between the two. The ring is able to move axially, independently of the faceplate and the ostomy pouch. In order to allow the ring to "float", a wearer is required to connect together each component of the ostomy device prior to use. This is not practical for users with limited manual dexterity and limits the convenience of such a device. Furthermore, the belt attachment ring is relatively stiff in comparison to the adhesive faceplate and bruising and skin damage are caused by the belt-attachment tabs pressing against a wearer in use, especially at the point of attachment of the belt.

The present invention sets out to provide an ostomy bag with an improved belt-attachment mechanism that overcomes or at least alleviates the problems described.

In one aspect, the invention provides an ostomy device comprising an ostomy bag; a peristomal pad with a body-side adhesive surface and at least one belt attachment means interposed between the ostomy bag and a bag-side surface of the peristomal pad, wherein the device comprises at least one skin protection means.

Preferably, the skin protection means comprises an area of the peristomal pad configured to conceal thereunder the or each belt attachment means.

By ensuring that the belt attachment means does not contact a wearer's skin during use, the risk of skin damage is greatly reduced. The shape of the peristomal pad ensures that the skin is cushioned from the pressure of the or each belt attachment means.

Preferably, the skin protection means comprises an elongate belt-receiving loop.

The belt-attachment means of the present invention is convenient for a user, and is secure and comfortable. The elongate shape of the belt-attachment means ensures that no dangerous pressure points are created, because pressure is spread along the length of the loop. This avoids the possibility of the belt attachment causing skin damage, such as, bruising or sores.

Preferably, the or each elongate belt loop comprises a plastic material.

More preferably, the or each belt attachment means comprises a flexible film.

Preferably, the flexible film is positioned between the or each belt attachment means and an opening in the peristomal pad.

The flexible film portion of the belt attachment means reduces the risk of skin damage, is moveable with respect to the peristomal pad and allows the belt loops to be cut off.

Preferably, each attachment means is tack-welded to the peristomal pad.

Tack welding ensures a smooth connection profile between the attachment means and the peristomal pad. This reduces the risk of pressure points and discomfort or skin damage to a wearer.

Preferably, the ostomy device further comprises a belt, wherein each end of the belt comprises a length of hook and loop fastening material.

Hook and loop fastening material, such as Velcro, allows a belt to be secured to the ostomy device without creating any pressure points at the point of attachment.

Preferably, the belt comprises a length of loop fastening material with a tab of hook fastening material at each end.

The hook fastening material is comfortable to be positioned against a wearer's skin.

The invention will now be described by way of example with reference to the accompanying diagrammatic drawings, in which.

Figure 1:
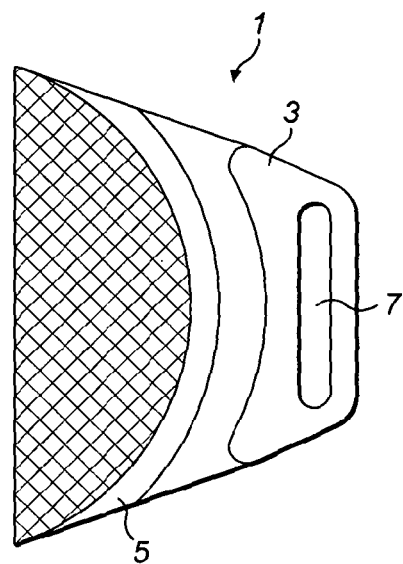
FIG. 1 is a plan view of a single attachment member constructed in accordance with the present invention.
Figure 2:
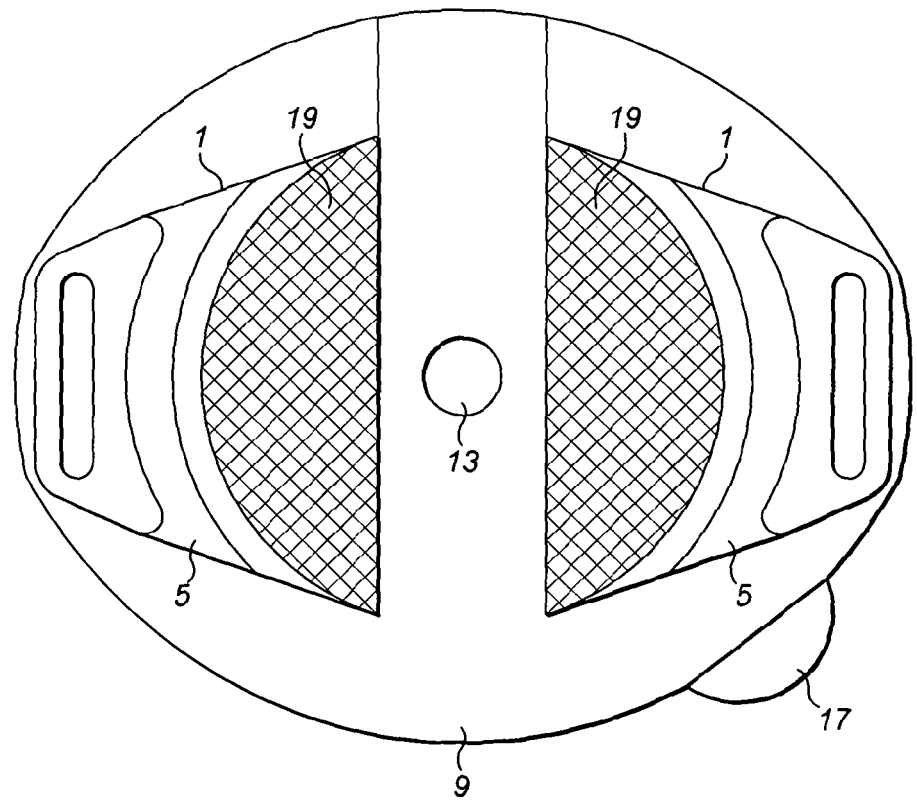
FIG. 2 is a plan view of the attachment member of the present invention shown with the overlying peristomal pad.

Referring first to FIGS. 1 and 2, the belt attachment member 1 of the present invention comprises a plastic belt-receiving loop 3 over-moulded onto a highly flexible film 5. The belt-receiving loop 3 is made of polyethylene and has a thickness of around 1.50 mm. It is to be understood that the "loop" can be of any shape or configuration, depending on the belt that is to be threaded therethrough. In the embodiment shown in FIG. 1, the "loop" 3 comprises a rectangular aperture 7 of length 30 mm and width 4 mm.

Figure 3:
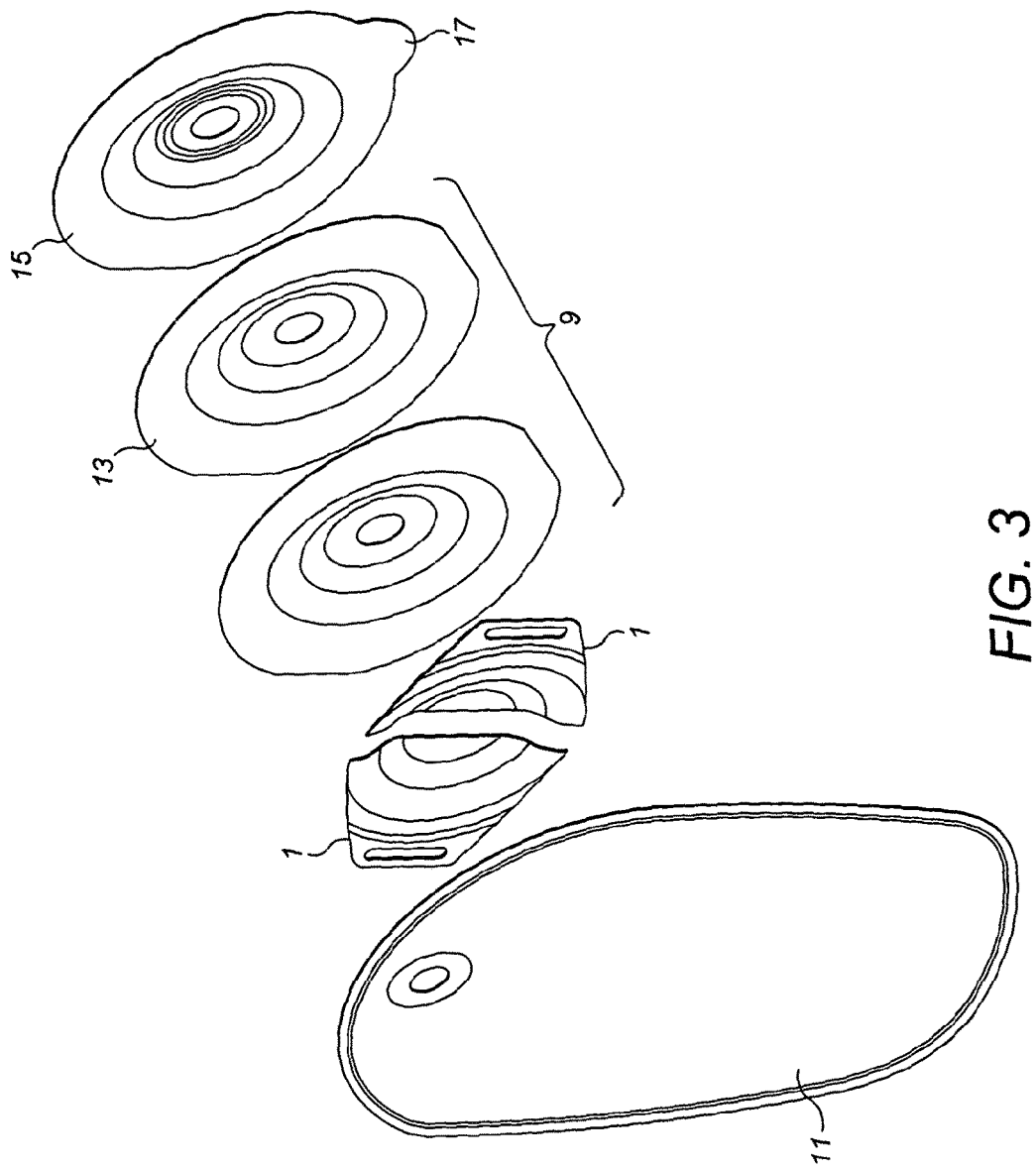
FIG. 3 is an exploded perspective view of the attachment member of FIGS. 1 and 2 together with the further components of an ostomy appliance.

Referring to FIGS. 2 and 3, showing a one-piece ostomy device, the belt attachment members 1 are sandwiched between a peristomal pad 9 and the ostomy pouch 11. The opening of the ostomy pouch (not shown) is aligned with an opening 13 in the peristomal pad, through which waste can pass when the device is in use. The peristomal pad 9 is a substantially oval shape and has an adhesive layer 13 on its body-side surface. Prior to use, the adhesive layer 13 is covered by a release liner 15. The release liner has a tab 17 to assist in gripping the release liner 15 when it is removed to expose the adhesive layer 13 thereunder.

As shown in FIG. 2, a belt attachment member 1 is attached on each of two opposing sides of the peristomal pad 9. The shape of the peristomal pad 9 is such that the belt attachment member 1 is concealed behind the pad 9, in use. The flexible film 5 of the belt attachment member 1 is tack welded to the peristomal pad 9, as illustrated by the shaded area 19. The peristomal pad 9 is then heat-sealed or compression-sealed to the ostomy pouch 11. As shown in FIG. 3, the attachment members 1 are "over-moulded" and trapped between the ostomy pouch 11 and the peristomal pad 9.

Figure 4:
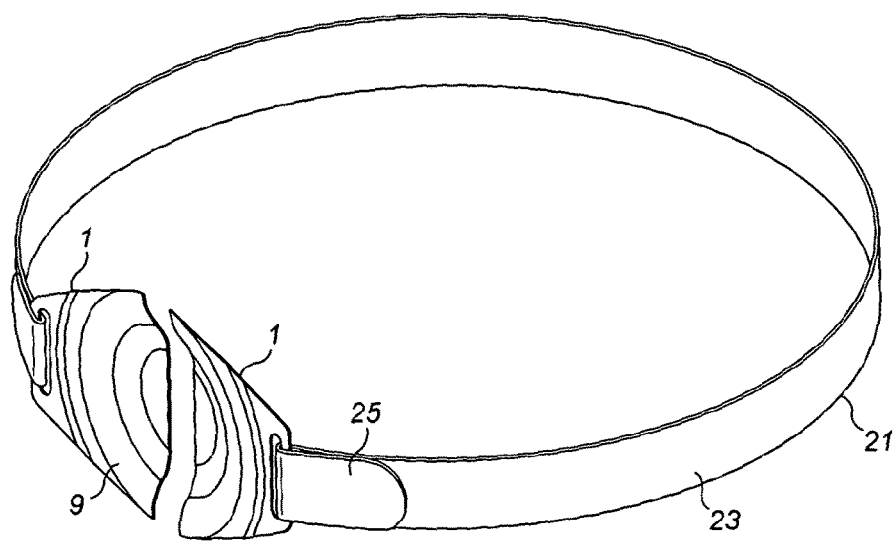
FIG. 4 is a perspective view of the attachment member of FIG. 2 with a belt attached.
Figure 5:
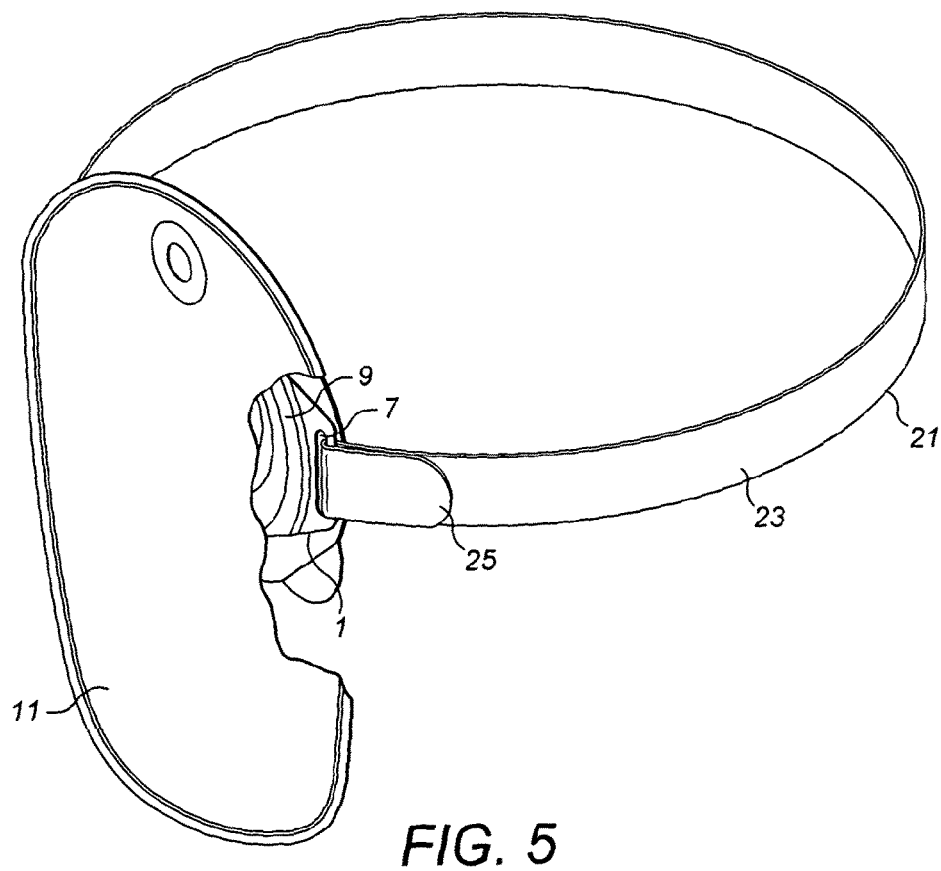
FIG. 5 is a perspective view showing the ostomy device, including the attachment members and a belt attached.

In use the release liner 15 is removed to expose the adhesive layer 13 on the body-side surface of the peristomal pad 9. The pad 9 is positioned by a wearer to attach the ostomy device around their stoma. Referring to FIGS. 4 and 5, to further secure the device, each end of a belt 21 is threaded through the aperture 7 of one of the belt attachment members 1. The belt 21 is folded back on itself at each of its ends around the belt loop 3 and secured by means of a hook and loop fastener material, such as Velcro™. In the embodiment shown, the length of the belt 23 comprises a loop material and an elongate tab 25 at each end of the belt 21 comprises a hook material. This allows a wearer to comfortably and securely attach the belt 21 to the ostomy appliance. When the belt 21 is attached around the wearer, any pressure at the point of attachment to the belt 21 is spread along the tab portion 25. The belt-receiving loops 1 are covered on the body-facing surface by the peristomal pad 9. The peristomal pad 9 and the deformable belt material cushion a wearer's skin from the belt-receiving loops 3. This prevents the risk of any skin damage caused by pressure from the belt-receiving loops 3. After use, the flexible film portion 5 of the belt attachment member 1 can be cut to remove the belt-receiving loops 3 or the belt 21 can simply be released and removed from the loops 3.

The above described embodiment has been given by way of example only, and the skilled reader will naturally appreciate that many variations could be made thereto without departing from the scope of the present invention.

The invention claimed is:

1. An ostomy device, comprising an ostomy bag comprising
 a distal side wall and a body-side wall comprising a body-side opening;
 a peristomal pad comprising
 a concave, distal, bag-side surface;
 a convex, body-side, adhesive surface with a central aperture that is configured to sealingly adhere and conform to a peristomal area around a stoma;
 first and second concave attachment areas on the concave, distal, bag-side surface of the peristomal pad on opposite sides of the body-side opening; and
 a skin protection means; and
 a belt attachment means comprising:
 first and second belt receiving loops attached to opposite ends of:
 a film with a center hole; and
 third and fourth convex attachment areas on the proximal surface of the belt attachment means on opposite sides of the center hole;
 wherein the belt attachment means is configured to be interposed, and sealingly attached, between the ostomy bag and the bag-side surface of the peristomal pad around the body side opening aligned with the central aperture and the center hole; and
 wherein the first and third and second and fourth attachment areas are tack-welded to each other by a plurality of tack welds; and
 wherein the skin protection means is configured to protect the peristomal area from the body-side surface of the first and second belt loops.

2. The ostomy device according to claim 1 wherein the skin protection means comprises an area of the peristomal pad configured to conceal thereunder the or each belt attachment means.

3. The ostomy device according to claim 1 wherein the belt attachment means comprises an elongate belt-receiving loop.

4. The ostomy device according to claim 3 wherein the elongate belt-receiving loop comprises a plastic material.

5. The ostomy device according to claim 3 wherein the or each elongate belt-receiving loop comprises a flexible film.

6. The ostomy device according to claim 1 further comprising a belt wherein each end of the belt comprises a length of hook and loop fastening material.

7. The ostomy device according to claim 6 wherein the belt comprises a length of loop fastening material with a tab of hook fastening material at each end.

* * * * *